United States Patent [19]

Narisada et al.

[11] Patent Number: 4,525,355
[45] Date of Patent: Jun. 25, 1985

[54] 7-β-UREIDOACETAMIDO-OXACEPHALOS-PORINS

[75] Inventors: Masayuki Narisada, Ibaraki; Fumihiko Watanabe, Osaka; Tetsuo Okada, Sakai; Hiromu Matsumura, Ashiya, all of Japan

[73] Assignee: Shionogi & Co., Ltd., Osaka, Japan

[21] Appl. No.: 566,023

[22] Filed: Dec. 27, 1983

[30] Foreign Application Priority Data

Dec. 27, 1982 [JP] Japan .................. 57-229358

[51] Int. Cl.³ .................. A61K 31/535; C07D 498/04
[52] U.S. Cl. ........................ 514/210; 544/90
[58] Field of Search ............... 544/90; 424/248.51, 424/248.52

[56] References Cited

U.S. PATENT DOCUMENTS 4,232,151 11/1980 Nagata et al. .................. 544/90
4,371,532 2/1983 Narisada et al. ............... 424/248.51

Primary Examiner—Richard L. Raymond
Attorney, Agent, or Firm—Wenderoth, Lind & Ponack

[57] ABSTRACT

A 7β-ureidoacetamido-7α-methoxy-3-(1-carbamoylmethyl-1H-tetrazol-5-yl)thiomethyl-1-dethia-1-oxa-3-cephem-4-carboxylic acid derivative represented by the following formula:

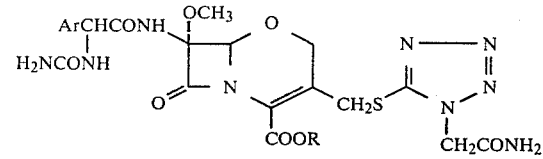

wherein Ar is phenyl, hydroxyphenyl, or thienyl and R is hydrogen, a light metal, or a carboxy-protecting group.

7 Claims, No Drawings

7-β-UREIDOACETAMIDO-OXACEPHALOSPORINS

The present invention relates to 7β-(2-aryl-2-ureidoacetamido)-7α-methoxy-3-(1-carbamoylmethyl-1H-tetrazol-5-yl)thiomethyl-1-dethia-1-oxa-3-cephem-4-carboxylic acid derivatives represented by the formula (I) below, their therapeutical use, processes for preparing them and pharmaceutical compositions containing them:

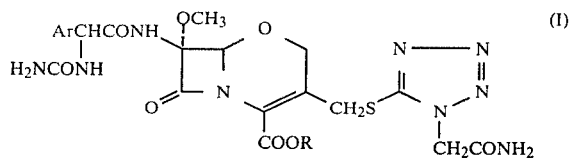

wherein Ar is phenyl, hydroxyphenyl, or thienyl and R is hydrogen, a light metal, or a carboxy-protecting group.

In the above definitions, the term "light metal" denotes a metal belonging to the second to forth period of the groups I to III in the periodic table, which provides a physiologically acceptable ion in the body fluid. Lithium, sodium, potassium, magnesium and calcium are representative of the light metal.

The term "carboxy-protecting group" refers to those commonly employed in the cephalosporin art to protect the carboxyl group at the 4-position without adversely affecting the β-lactam ring. Illustrative of these protecting groups are alkyl and aralkyl each optionally substituted by nitro, alkoxy, aryl, halogen or acyloxy. Specific examples are benzyl, p-nitrobenzyl (abbrev. PNB), p-methoxybenzyl (abbrev. PMB), benzhydryl (abbrev. BH), tert.-butyl, pivaloyloxymethyl (abbrev. POM), trichloroethyl (abbrev. TCE), methoxymethyl, acetoxymethyl, etc. Trialkylsilyl groups are also included.

The compounds (I) of the present invention exhibit a strong antibiotic activity to various microorganisms and, also to those resistant to other antibiotics.

Thus, the compounds (I) are valuable antibiotics against various Gram positive and negative bacteria, and useful as drugs for human and veterinary uses. They can be used for treating or preventing infections caused by Gram positive bacteria (e.g. *Staphylococcus aureus, Streptococcus pyogenes, Bacillus subtilis, Bacillus cereus, Diplococcus pneumoniae, Corynebacterium diphtheriae*) and Gram negative bacteria (e.g. *Escherichia coli, Klebsiella pneumoniae, Proteus mirabilis, Proteus vulgaris, Proteus rettgeri, Proteus morganii, Enterobacter cloacae, Shigella sonnei, Salmonella paratyphi, Salmonella typhi, Serratia marsescens*), including anaerobic bacteria (e.g. *Bacteroides fragilis, Eubacterium lentum*). The compounds can be used also as disinfectants for preventing decay of perishables, additives to foodstuffs, or preventing bacterial growth of hygenical materials.

The compounds (I) can be used in a wide variety of oral or parenteral dosage forms solely or in admixture with other coacting substances. The pharmaceutical compositions may be a mixture of 0.01 to 99% of compound (I) with a pharmaceutical carrier which can be a solid material or liquid material in which the compounds are dissolved, dispersed, or suspended. They can be in a unit dosage form. The solid compositions can take the form of tablets, powder, dry syrup, troches, granules, capsules, pills, suppositories, or like solid preparations. The liquid compositions can take the forms of injections, ointments, dispersions, inhalant, suspensions, solutions, emulsions, syrups, or elixirs. They may be flavored, colored, and tablets, granules, and capsules may be coated.

All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium alginate, tragacanth, carboxymethylcellulose, syrup, sorbitol, polyvinylpyrrolidone); disintegrators (e.g. starch, agar, carbonates, sodium laurylsulfate); lubricant (e.g. stearic acid, talc, paraffin, boric acid, silica, sodium benzoate, polyethylene glycol, cacao oil, magnesium stearate); emulsifying agents (e.g. lecithin, sorbitan monooleate, glycerin dioctanoate, acacia); suspending agents (e.g. sorbitol, methyl cellulose, glucose, sugar syrup, gelatin, hydroxyethylcellulose, carboxymethylcellulose, aluminum stearate gel, hydrogenated fats); solvents (e.g. water, buffer, peanut oil, sesame oil, methyl oleate); preservatives (e.g. methyl or ethyl p-hydroxybenzoate, sorbic acid); edible coloring agents, aromatic substances, solubilizing agents, buffers, stabilizing agents, analgesics, dispersing agents, wetting agents, antioxidants, and the like can be used if the agents do not exert adverse effect on the compounds, according to the methods conventional in the art.

Compounds (I) having a carboxylic acid salt group are soluble in water, and conveniently used as solution for oral administration or intravenus, intramuscular, or subcutaneous injection according to a conventional method. The compounds can be dissolved in aqueous or oily solvents for injection to give a solution in an ampoule, but generally, more prolonged storage are possible by making a vial preparation containing crystals, powder, microcrystals, or lyophilizate of compound (I), and dissolving or suspending the drug before use with the said solvents for injection. The vial preparation or injection can be given to a patient at a daily dose of e.g. 0.2 to 5 g depending on the infected bacteria, condition of the patient, and interval of the administration.

Compounds (I), being a pharmaceutically acceptable ester (e.g. indanyl, acetoxymethyl, pivaloyloxymethyl, ethoxycarbonyloxyethyl, phenacyl, phthalidyl, phenyl, tolyl, xylyl, methoxyphenyl esters), can be absorbed through the digestive organ to some extent, and can be administered to human or veterinary subjects as powder, tablets, granules, capsules, dry syrup, emulsions, solution, suspension, and like oral preparations. They may be pure compounds or a composition comprising compounds (I) and said pharmaceutical carriers. The preparation can be made according to the methods conventional in the art, and can be administered to a patient at a daily dose of e.g. 1 to 2 g depending on the condition of the patient and the diseases.

This invention also provides a method for treating or preventing human or veterinary bacterial infections by administering to the human or animal subject an effective amount of compound (I) at a daily dose of e.g. 0.2 to 5 g for injection or e.g. 1 to 2 g for oral administration, or 10 μg to 1 g for topical application, at an interval of e.g. 3 to 12 hours.

The method is applicable for treating or preventing some diseases caused by bacteria sensitive to compounds (I) e.g. pneumonia, bronchitis, pneumonitis, empyema, nasopharyngitis, tonsillitis, rhinitis, dermatitis, pustulosis, ulceration, abses, wound and soft tissue infections, ear infections, osteomyelitis, septicemia, gastroenteritis, enteritis, respiratory or urinary tract infections, and pyelonephritis when caused by bacteria sensitive to compound (I).

Preferably the compounds (I) are given to a patient in forms of pharmaceutical preparations e.g. powder, dry syrup, tablets, troches, granules, capsules, pills, suppositories, injections, ointments, dispersions, inhalant, suspensions, solutions, emulsions, syrups, and elixirs. They may be in a unit dosage form e.g. tablets, troches, capsules, injections, vials, granules or powder in a separate container or package.

All of the pharmaceutical preparations listed above can be prepared in a conventional manner.

It will be readily understood to those in the art that the compounds (I) can also be used as germicides or anticeptics. In addition, they are useful as a starting material for preparing some other compounds of the formula (I) and as an antibiotic agent for testing the sensitivity of microorganisms.

Preferred compounds (I) of the invention are those wherein Ar is phenyl or hydroxyphenyl, R is hydrogen, sodium, potassium, diphenylmethyl, p-methoxybenzyl, phthalidyl, 2-oxo-dioxolenylmethyl, acetoxymethyl, 1-(ethoxycarbonyloxy)ethyl or pivaloyloxymethyl.

The compounds of the formula (I) can be prepared by various methods detailed below:

1. Preparation of salts

The reaction of the compound (I) wherein R is hydrogen with a base or a salt of a weaker carboxylic acid results in the compound (I) wherein R is a light metal. The reaction may be carried out according to a conventional method known to the art. Preferred methods are the neutralization of the free acid (I) with a light metal bicarbonate. Alternative method is the exchange reaction of the free acid (I) with a salt of a lower carboxylic acid in a polar organic solvent such as alcohol, ketone or ester, followed by the addition of a solvent to which the desired salt (I) is sparingly soluble.

The above reactions complete after one to ten minutes when carried out at a temperature below 50° C. If necessary, the reaction mixture can be kept for a longer time unless any side reaction occurs.

2. Elimination of carboxy-protecting group

The compounds of the formula (I) wherein R is a carboxy-protecting group can be converted to the compounds (I) wherein R is hydrogen according to any of the conventional deprotecting reactions described below.

In the following description, the carboxy-protecting group will be sometimes represented by the name corresponding to the group formed by the reaction between the carboxylic acid and the compound employed for protecting the carboxylic acid, only for the purpose of avoiding the complexity of description. Thus, the protecting group "R" contained in the moiety of the formula:

—COOR will be referred to as "ester" for convenience.

(a) The compounds (I) having highly reactive protecting groups can be deprotected by contact with an acid, a base, a buffer or an ion exchange resin in an aqueous solution. Less reactive protecting such as trichloroethyl or p-nitrobenzyl can be eliminated by treating it with a combination of a metal and a acid or with dithionate, or by a catalytic reduction.

(b) Aralkyl esters can be eliminated by a hydrogenation using, e.g., platinum, palladium or nickel as a catalyst.

(c) Aralkyl esters and cyclopropylmethyl esters can be eliminated using a mineral acid, such Lewis acid as aluminum trichloride, tin tetrachloride or titanium tetrachloride, a sulfonic acid such as methanesulfonic acid and trifluoromethanesulfonic acid, or a strong carboxylic acid such as trifluoroacetic acid, and if necessary, in the presence of a cation scavenger.

(d) The other conventional processes known for deprotecting carboxy-protecting groups can be employed in the present invention.

3. Introduction of a tetrazolylthio group

The compounds (I) of the invention can be obtained by the reaction between the compound represented by the formula (II) below and 1-substituted tetrazole-5-thiol of the formula (III) or its reactive derivative;

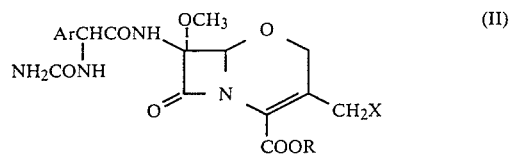

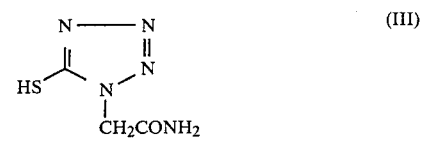

wherein Ar and R are as defined above and X is a leaving group. Preferred leaving groups are halogen and acyloxy having a high activity such as sulfonyloxy. The preferred reactive derivatives of the tetrazole-5-thiol are an alkali or alkaline earth metal salt and a tetraalkylammonium salt of the thiol (III).

4. Amidation

The compounds of the formula (I) can be prepared by reacting the amine compound of the formula (IV):

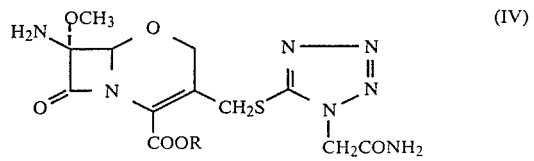

wherein R is as defined above, or a reactive derivative thereof with a substituted acetic acid of the formula (V):

wherein Ar is as defined above, or its reactive derivative.

The reaction between the compound (IV) and the compound (V) is conducted in different manners as explained below depending on the nature of the reactants.

(a) Free acids

The amine (IV) or its derivative is reacted with the properly substituted acetic acid (V) or its derivative in the presence of a condensing agent, e.g., carbodiimide, carbonyldiimidazole, isoxazolium salt, acylamino compound, phosphorus halogenide, cyanuric halogenide, sulfonyl chloride, phosphorus oxychloride, thionyl chloride, amidase, etc., to give the compound (I) of the invention.

(b) Acid anhydride derivatives

The acid anhydride derivative of the compound (V) can be reacted with the amine (IV) in the presence of an acid scavenger such as an organic or inorganic base, oxirane, an amide, an adsorbent, or the like, to give the compound (I). The acid anhydrides employed in the reaction include symmetric anhydrides of the acids (V), mixed anhydrides of the acid (V) with either a mineral acid or an organic acid such as other carboxylic acid or sulfonic acid, intramolecular anhydrides such as ketene, 2-amino-4-Ar-5-oxazolinone, etc.

(c) Acid halide derivatives

The acid halide derivative of the compound (V) can be reacted with the amine (IV) or its reactive derivative in the presence of an acid scavenger selected from those mentioned in the above item (b) to give the compound (I). An aqueous solvent can be employed in this reaction.

(d) Activated ester and amide derivatives

The activated ester or amide derivative of the compound (V) is reacted with the amine (IV) in an organic solvent, preferably in an aprotic organic solvent, to obtain the compound (I).

Examples of the activated esters and amides employed in this reaction are enol esters, aryl esters, esters formed with a hydroxy heterocycle containing nitrogen atom(s) in the ring, esters formed with an N-hydroxy compound, thiol esters, amides with a heterocycle such as imidazole, amides formed with 2-alkoxy-1,2-dihydroquinoline, diacylanilides, formimino compounds, etc.

Other conventional amidation reactions known per se can be employed for the preparation of the compounds (I).

In the above reactions stated in 4-(a) to (d), typical reactive derivatives of the amine (IV) are those wherein the amino group at the 7-position has been activated by a silyl radical such as trialkylsilyl or alkoxydialkylsilyl, a metal oxycarbonyl radical, an alkoxyphosphinyl radical, an enamine radical, etc. In addition, the reactive derivatives include the amines (IV) wherein the amino group has been substituted by 1-haloalkylidene, 1-alkoxyalkylidene, 1-haloaralkylidene, 1-alkoxyaralkylidene, 1-acyloxyaralkylidene, alkylidene or substituted alkenyl radical.

5. Protection of carboxylic acid and other reactive functional groups

In carrying out the foregoing various reactions or in converting the compound (I) to the other compound (I), it may be sometimes necessary to protect reactive functional groups other than the reacting group involving in the intended reaction.

For this purpose, a variety of conventional techniques for the protection are all applicable to the processes of the invention. Such techniques are, for example, disclosed in the literatures, such as J. F. W. McOmie Ed., "Protective Groups in Organic Chemistry", pp183, PLEUM Press, N.Y., 1973; S. Patai, Ed., "The Chemistry of Functional Groups", pp505, Interscience Publ., John Wiley & Sons Ltd. London, 1969; and Flynn Ed., "Cephalosporins and Penicillins", Academic Press, N.Y. 1972. Typical examples of the protection of reactive functional groups are acylation, enamination and silylation for an amino group, and esterification, amidation and acid anhydridation for a carboxylic acid.

It should be noted that the term "protection of carboxylic acid" herein used also refers to the esterification of the carboxylic acid at 4-position for the purpose of obtaining a pharmacologically active ester. The esterification of the compound (I) having a free carboxylic acid can be conducted by neutralizing the acid with a base to form a carboxylate, and treating the latter with an acid halide having a proper ester residue.

6. Reaction Conditions

Most of the reactions listed in the above items 1. to 5. are usually carried out at a temperature between $-30°$ and $100°$ C., particularly, between $-20°$ and $50°$ C., for 10 minutes to 10 hours in a proper solvent, and if necessary, under anhydrous conditions.

Examples of the solvent employable in the processes of this invention are the following: hydrocarbons (e.g. pentane, hexane, octane, benzene, toluene, xylene), halogenated hydrocarbons (e.g. dichloromethane, chloroform, carbon tetrachloride, dichloroethane, trichloroethane, chlorobenzene), ethers (e.g. diethylether, methyl isobutyl ether, dioxane, tetrahydrofuran), ketones (e.g. acetone, methyl ethyl ketone, cyclohexanone), esters (e.g. ethyl acetate, isobutyl acetate, methyl benzoate), nitro hydrocarbons (e.g. nitromethane, nitrobenzene), nitriles (e.g. acetonitrile, benzonitrile), amides (e.g. formamide, acetamide, dimethylformamide, dimethylacetamide, hexamethylphosphorotriamide), sulfoxides (e.g. dimethyl sulfoxide), carboxylic acids (e.g. formic acid, acetic acid, propionic acid), organic bases (e.g. diethylamine, triethylamine, pyridine, picoline, collidine, quinoline), alcohols (e.g. methanol, ethanol, propanol, hexanol, octanol, benzyl alcohol), water, other industrially available solvents and a mixture thereof.

An ultimate product (I) of the invention can be isolated from the reaction mixture by any of, or a combination of, the conventional methods such as absorption, elution, distillation, precipitation, concentration, chromatography and the like, after the removal of impurities such as starting materials, by-products and solvents by conventional techniques such as extraction, evaporation, washing, filtration, drying, etc.

Specific preferred examples of the compounds (I) of the invention are as follows especially D-isomers at the 7-side chain:

diphenylmethyl 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylate, 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylic acid, sodium 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylate, p-methoxybenzyl 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylate, pivaloyloxymethyl 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylate, 7β-(2-phenyl-2-ureidoacetamido)-7α-methoxy-3-(1-carbamoylmethyl-1H-tetrazol-5-yl)thiomethyl-1-dethia-1-oxa-3-cephem-4-carboxylic acid, diphenylmethyl 7β-(2-phenyl-2-ureidoacetamido)-7α-methoxy-3-(1-carbamoylmethyl-1H-tetrazol-5-yl)thiomethyl-1-dethia-1-oxa-3-cephem-4-carboxylate, sodium 7β-(2-phenyl-2-ureidoacetamido)-7α-methoxy-3-(1-carbamoylmethyl-1H-tetrazol-5-yl)thiomethyl-1-dethia-1-oxa-3-cephem-4-carboxylate, 7β-[2-(p-hydroxyphenyl)-2-ureidoacetamido]-7α-methoxy-3-(1-carbamoylmethyl-1H-tetrazol-5-yl)thiomethyl-1-dethia-1-oxa-3-cephem-4-carboxylic acid, diphenylmethyl 7β-[2-(p-hydroxyphenyl)-2-ureidoacetamido]-7α-methoxy-3-(1-carbamoylmethyl-1H-tetrazol-5-yl)thiomethyl-1-dethia-1-oxa-3-cephem-4-carboxylate, and sodium 7β-[2-(p-hydroxyphenyl)-2-ureidoacetamido]-7α-methoxy-3-(1-carbamoylmethyl-1H-tetrazol-5-yl)thiomethyl-1-dethia-1-oxa-3-cephem-4-carboxylate.

Especially preferred compounds are:

7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylic acid, sodium 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylate, pivaloyloxymethyl 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylate, 7β-(2-phenyl-2-ureidoacetamido)-7α-methoxy-3-(1-carbamoylmethyl-1H-tetrazol-5-yl)thiomethyl-1-dethia-1-oxa-3-cephem-4-carboxylic acid, and sodium 7β-(2-phenyl-2-ureidoacetamido)-7α-methoxy-3-(1-carbamoylmethyl-1H-tetrazol-5-yl)thiomethyl-1-dethia-1-oxa-3-cephem-4-carboxylate.

Practical and presently preferred embodiments of the invention are illustratively shown in the following Preparation and Examples where Infra Red (IR) and Nuclear Magnetic Resonance (NMR) data are shown by ν(cm⁻¹) and δ(ppm) values (coupling constant J in Hz) respectively and following abbreviations are employed: Me(=methyl), Bu(=butyl), Ph(=phenyl), THF(=tetrahydrofuran), DMF(=dimethylformamide), BH(=benzhydryl), PMB(=p-methoxybenzyl), POM(=pivaloyloxymethyl), mM(=millimole), HP-20(32 Diaion HP-20, trade name of styrene divinylbenzene copolymer produced by Mitsubishi Kasei Co., Ltd., Japan).

Preparation 1 Diphenylmethyl 7β-amino-7α-methoxy-3-(1-carbamoylmethyl-1H-tetrazol-5-yl)thiomethyl-1-dethia-1-oxa-3-cephem-4-carboxylate.

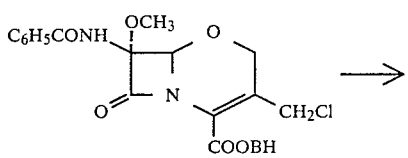

[a]

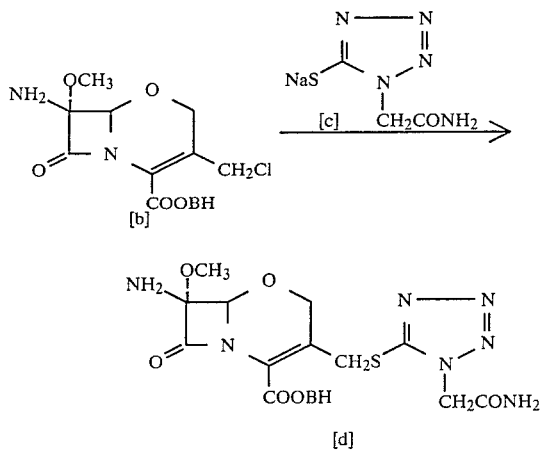

The compound of the formula [b], which has been prepared from the compound [a] (16.4 g, 30 mM) according to a conventional method, is dissolved in dichloromethane (60 ml). To the solution is added, while ice-cooling, a solution of the sodium salt of 1-carbamoylmethyl-tetrazole-5-thiol of the formula [c] (4.8 g) dissolved in DMF (20 ml) and the mixture is stirred for 30 minutes. The reaction mixture is poured into water and extracted with ethyl acetate. The extract is washed with water three times and evaporated in vacuo to remove the solvent. The residue is chromatographed over silica gel using ethyl acetate containing 1% of acetonitrile as the eluent. Evaporation of the eluate gives the title compound of the formula [d]. Yield: 6.3 g.

IR(CHCl₃): 3370, 1770, 1710 cm⁻¹.

NMR(CDCl₃): 2.28(brs, 2H), 3.45(s,3H), 4.05–4.25(m, 2H), 4.42–4.63(m,2H), 4.78(brs,2H), 4.82(s,1H), 6.02–6.45(m,2H), 6.82(s,1H), 7.05–7.68(m,10H).

EXAMPLE 1

Diphenylmethyl 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylate [Compound No. 3].

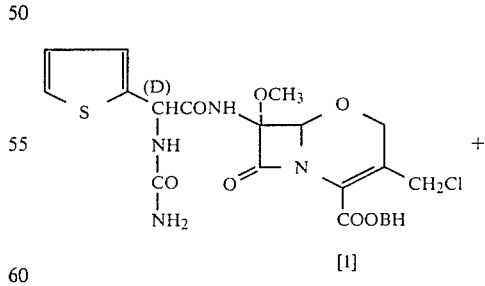

[1]

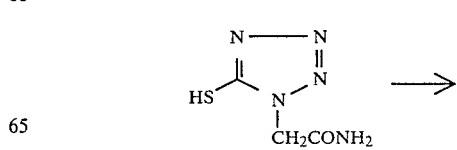

[2]

-continued

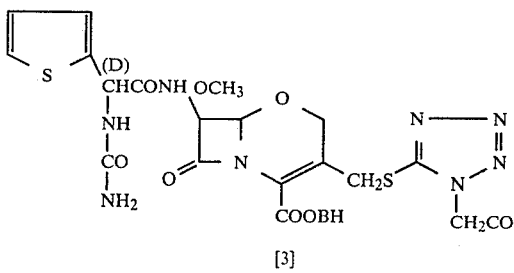

[3]

The compound of the formula [1] (521 mg, 2×1.64 mM) is dissolved in dimethylformamide (DMF) (6 mM). To the solution is added 473 μl of a solution of sodium methylate in methanol (5.2 M/L) (1.5×1.64 mM) while ice-cooling and the mixture is stirred for 10 minutes. The compound of the formula [2] (1.0 g, 1.64 mM) is added to the mixture, and stirring is continued for ten minutes. The reaction mixture is poured into water and extracted with methyl ethyl ketone. The extract is washed with 5% aqueous $NaHCO_3$ solution and water, dried over anhydrous magnesium sulfate, and concentrated under reduced pressure. The resulting residue is crystallized from acetone/ether to give the title compound of the formula [3]. Yield: 1.18 g (98%). m.p.>140° C.

IR(Nujol): 3458, 3360, 3185, 1779, 1694, 1654, 1599, 1536 $cm^{-1}$.

NMR(d6-Acetone): 3.49(s,3H), 4.16(ABq-A part,J=13.5,1H), 4.35(ABq-B part,J=13.5,1H), 4.53(s,2H), 5.12(s,3H), 5.62(s,2H), 6.13(d,J=9,1H), 6.76–7.70(m,18H), 9.10(s,1H).

Elementary Analysis $(C_{32}H_{31}O_8N_9S_2 \cdot \frac{1}{3}(C_2H_5)_2O \cdot \frac{1}{2} H_2O)$

|  | C | H | N | S |
|---|---|---|---|---|
| Calculated (%): | 52.16 | 4.64 | 16.43 | 8.36 |
| Found (%): | 51.85 | 4.58 | 16.29 | 8.42 |

EXAMPLE 2

7β-[2-(2-Thienyl)-2-ureidoacetamido]-7α-methoxy-3-(1-carbamoylmethyl-1H-tetrazol-5-yl)thiomethyl-1-dethia-1-oxa-3-cephem-4-carboxylic acid [Compound No. 4].

[3] ⟶

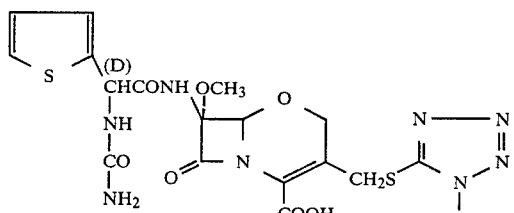

[4]

The diphenylmethyl ester [3] (1.12 g) obtained in Example 1 is dissolved in methylene chloride (8 ml). To the solution are added anisole (3 ml) and trifluoroacetic acid (3 ml) while ice-cooling and the mixture is stirred for 30 minutes. The reaction mixture is concentrated in vacuo. The residue is washed with ethyl ether to provide the desired carboxylic acid of the formula [4] as a powder.

Yield: 900 mg.

IR(Nujol): 3310, 3180, 1775, 1680 $cm^{-1}$.

NMR($CD_3OD$): 3.50(s,3H), 4.23(s,2H), 4.47(s,2H), 5.06(s,1H), 5.13(s,2H), 5.71(s,1H), 6.88–7.39(m,3H).

EXAMPLE 3

Sodium 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylate [Compound No. 5].

[4] ⟶

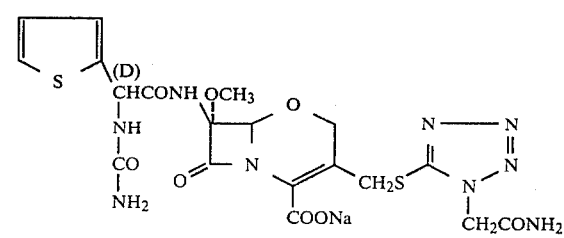

[5]

The carboxylic acid [4] (900 mg) obtained in Example 2 is dissolved in aqueous $NaHCO_3$ solution ($NaHCO_3$: 120 mg, $H_2O$: 15 ml). The resulting solution is washed with ethyl acetate to remove insoluble impurities. The aqueous layer is lyophilized to obtain the desired sodium salt of the formula [5]. Yield: 791 mg (87.6%, on the basis of the compound [3]).

IR(KBr): 3355, 1769, 1687(br), 1601, 1520 $cm^{-1}$.

UV($\lambda_{max}^{H2O}$): 233(ε: 15600), 269(ε: 10500)nm.

NMR($D_2O$: Ext.TMS): 3.96(s,3H), 4.52(ABq-A part,J=13.5,1H), 4.68(ABq-B part,J=13.5,1H), 4.69(Abq-A part,J=16.5,1H), 4.88(ABq-B part,J=16.5,1H), 5.57(s,1H), 5.73(s,2H), 6.09(s,1H), 7.40–7.90(m,3H).

$[\alpha]_D^{23.5}$: −53.3°±0.9(c=1.004, $H_2O$).

Elementary Analysis $(C_{19}H_{20}O_8N_9S_2Na \cdot 1.7H_2O)$

|  | C | H | N | S |
|---|---|---|---|---|
| Calculated (%): | 36.79 | 3.80 | 20.32 | 10.34 |
| Found (%): | 37.04 | 3.86 | 19.97 | 10.27 |

The sodium salt [5] (1 g) is dissolved in distilled water (4 ml) under sterile conditions. The solution can be administered to patients twice a day for the purpose of treating infections caused by Staphylococcus aureus.

Minimum inhibitory concentration value of the salt [5] on Streptococcus pyogenes is 0.1 μg/ml or below when measured according to the standard procedure of Nippon Kagaku Ryoho Gakkai (Japan Society of Chemotherapy).

EXAMPLE 4

Alternative process for preparing the carboxylic acid of the formula [4].

[3] ⟶

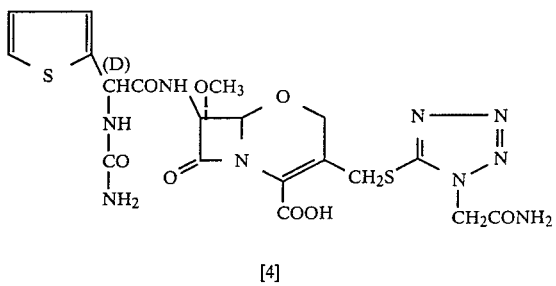

[4]

The powdery diphenylmethyl ester of the formula [3] (9.70 g, 13.22 mM) is added to a stirred mixture of aluminum chloride (5.45 g, 3×13.22 mM), anisole (30 ml) and nitromethane (80 ml) while ice-cooling, and the mixture is stirred for one hour. The reaction mixture is poured into aqueous NaHCO₃ solution (NaHCO₃: 22.2 g, H₂O: 150 ml). Precipitated aluminum hydroxide is filtered off by Hyflo Super Cel. The aluminum hydroxide cake on the filter is washed three times with water (each 150 ml), and the washings are combined with the filtrate. The aqueous layer is separated and washed twice with ethyl acetate and then once with methylene chloride. The aqueous solution is diluted with water to 1000 ml and adjusted to pH 2.2 with 10% hydrochloric acid. After decolorization with activated charcoal, the solution is degassed under reduced pressure and chromatographed over HP-20(160 ml). Fractions eluted with 20 to 40% acetone/water are combined and evaporated in vacuo to remove the acetone. The remaining aqueous layer is lyophilized to obtain the desired carboxylic acid [4]. Physico-chemical data of the compound are identical with those of Example 2.

EXAMPLE 5 p-Methoxybenzyl 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylate [Compound No. 6].

[5] ⟶

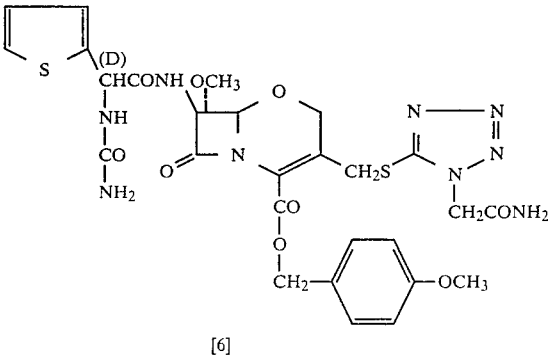

[6]

The sodium salt [5] (300 mg, 0.51 mM) obtained in Example 3 is dissolved in DMF(3 ml). p-Methoxybenzyl chloride (160 mg, 2×0.51 mM) and sodium iodide (200 mg, 2.6×0.51 mM) are subsequently added to the resultant solution, and the mixture is stirred for 2 hours at room temperature. The reaction mixture is poured into water and extracted with methyl ethyl ketone. The extract is washed successively with 5% aqueous NaHCO₃ solution and water, dried over anhydrous magnesium sulfate and evaporated in vacuo to remove the solvent. The residue is chromatographed over silica gel (water content: 10%). Fractions eluted with methyl ethyl ketone and those eluted with a mixture of chloroform and methanol (10:1) are combined and evaporated to dryness under reduced pressure. The residue is triturated with methanol and ethyl ether to obtain the title compound of the formula [6] as a powder. Yield: 193 mg (55%). m.p. 128°–131° C.

IR(KBr): 3440, 3360, 3200, 1781, 1690, 1660, 1612, 1516 cm⁻¹.

UV($\lambda_{max}^{MeOH}$: 228(ε: 27800), 275(ε: 11500), 280(ε: 11800)nm.

NMR(d-Acetone): 3.42(s,3H), 3.78(s,3H), 4.12(Abq-A part,J=13.5,1H), 4.41(ABq-B part,J=13.5,1H), 4.51(s,2H), 5.07(s,1H), 5.15(s,2H), 5.23(s,2H), 5.55(s,2H), 6.05(d,J=9,1H), 6.16–7.49(m,10H), 8.90(s,1H).

$[\alpha]_D^{24.5}$: $-86.2° \pm 1.3$(c=1.006, MeOH).

Elementary Analysis ($C_{27}H_{29}O_9N_9S_2 \cdot \frac{1}{2}H_2O$)

|  | C | H | N | S |
| --- | --- | --- | --- | --- |
| Calculated (%): | 46.54 | 4.34 | 18.10 | 9.20 |
| Found (%): | 46.41 | 4.49 | 18.01 | 8.92 | p-Methoxybenzyl ester [6] thus obtained gives corresponding carboxylic acid of the formula [4] by treating in the same manner as described in Example 4.

EXAMPLE 6

Pivaloyloxymethyl 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylate [Compound No. 7].

[5] ⟶

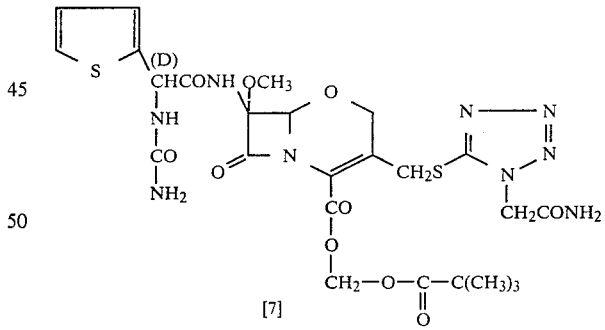

[7]

The carboxylic acid sodium salt [5] (400 mg, 0.68 mM) prepared in Example 3 is dissolved in DMF(4 ml). While ice-cooling, pivaloyloxymethyl iodide (189 μl, 1.5×0.68 mM) is added to the DMF solution and the mixture is stirred for 2 hours at room temperature. The reaction mixture is poured into water and extracted with methyl ethyl ketone. The extract is washed with 5% aqueous NaHCO₃ solution and water, dried over magnesium sulfate and concentrated in vacuo. The residue is purified by chromatography over silica gel. Fractions eluted with methyl ethyl ketone are combined and evaporated to dryness. The residue is triturated with methanol/ether to obtain the title compound of the formula [7] as powder. Yield: 317 mg (68.4%). m.p. 134°–137° C.

IR(KBr): 3425, 3360, 3200, 1783, 1747, 1692, 1658, 1530 cm$^{-1}$.

UV($\lambda_{max}^{MeOH}$): 232($\epsilon$: 15100), 283($\epsilon$: 9800)nm.

NMR(d-Acetone): 1.20(s,9H), 3.45(s,3H), 4.14(ABq-A part,J=13.5,1H), 4.46(ABq-B part,J=13.5,1H), 4.55(s,2H), 5.10(s,1H), 5.19(s,2H), 5.60(s,1H), 5.87(ABq-A part,J=6,1H), 6.03(ABq-B part,J=6,1H), 6.72–7.45(m,7H), 8.70(brs,1H), 9.01(s,1H).

$[\alpha]_D^{24.5}$: $-64.1° \pm 1.0$(c=1.014, MeOH).

Elementary Analysis (C$_{25}$H$_{31}$O$_{10}$N$_9$S$_2$·½H$_2$O)

|  | C | H | N | S |
|---|---|---|---|---|
| Calculated (%): | 43.46 | 4.67 | 18.25 | 9.28 |
| Found (%): | 43.47 | 4.72 | 18.10 | 9.22 |

EXAMPLE 7

7β-(2-Phenyl-2-ureidoacetamido)-7α-methoxy-3-(1-carbamoylmethyl-1H-tetrazol-5-yl)thiomethyl-1-dethia-1-oxa-3-cephem-4-carboxylic acid [Compound No. 15], and its diphenylmethyl ester [Compound No. 14] and sodium salt [Compound No. 16].

Part A

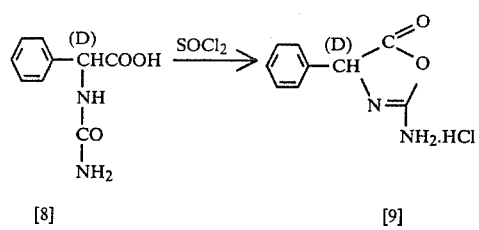

Part B

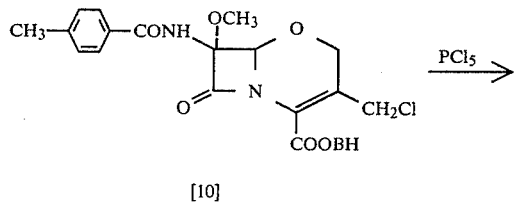

Part C

Part D

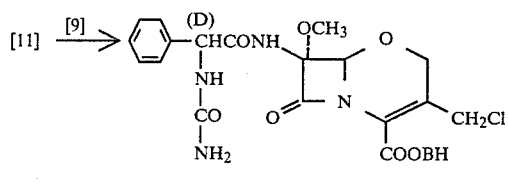

Part E

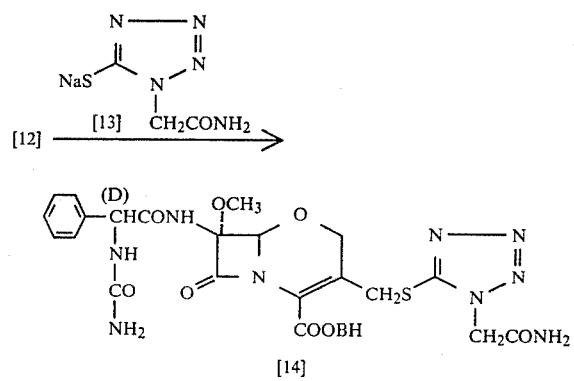

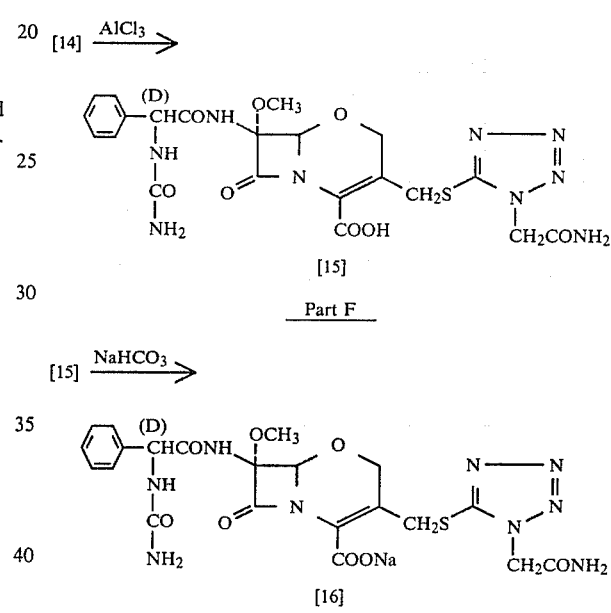

Part F

Part A The compound of the formula [8] (4.6 g, 1.3×18.28 mM) is suspended in acetonitrile (120 ml). To the suspension is added thionyl chloride (1.33 ml, 1.3×18.28 mM) at −10° C. and the mixture is stirred for one hour at this temperature. After completion of the reaction, ethyl ether is added to the mixture and precipitated compound of the formula [a] is collected and washed with ethyl ether. The compound is literally known.

Part B The compound of the formula [10] (10.0 g, 18.28 mM) is dissolved in methylene chloride (85 ml). To the solution are added while ice-cooling pyridine (2.66 ml, 1.8×18.28 mM) and phosphorus pentachloride (6.09 g, 1.6×18.28 mM), and the mixture is stirred at room temperature for one and half hours. The reaction mixture is then cooled to −50° C. Methanol (67 ml) cooled to −40° C. is added thereto and the mixture is stirred for 2 hours while ice-cooling. The mixture is cooled to −50° C. again, and a sodium methylate solution in methanol (5.2 M/L, 26 ml, 7.4×18.28 mM) is added thereto. Five minutes after completion of the addition, the reaction mixture is poured into a mixture of water and methylene chloride. Methylene chloride layer is separated, washed successively with 5% aqueous NaHCO$_3$ solution, water and saturated saline, and dried over anhydrous magnesium sulfate. The dried organic layer is filtered. Propylene oxide (2.47 ml, 2×18.28 mM) is added to the filtrate and the mixture is concentrated to about 80 ml under reduced pressure. A solution of the compound of the formula [11] in methylene chloride is thus obtained.

Part C To the solution obtained in Part B are added DMF (50 ml) and propylene oxide (2.47 ml, 2×18.28 mM). The resultant mixture is cooled to −50° C. and the compound [9] obtained in Part A (5 g, 1.3×18.28 mM) is added thereto. After being stirred for 30 minutes while ice-cooling, the reaction mixture is poured into a mixture of water and methylene chloride. The mixture is washed with 5% aqueous NaHCO3 solution and water, dried over anhydrous magnesium sulfate and concentrated under reduced pressure. The residue is purified by chromatography over silica gel. Fractions eluted with ethyl acetate are combined and worked up in a conventional manner to obtain the compound of the formula [12]. Yield: 3.45 g (31.3%, on the basis of the compound [10]).

IR(CHCl3): 3460, 3360, 3170, 1782, 1725, 1670, 1650 cm$^{-1}$.

Part D The compound of the formula [13] (630 mg, 1.2×3.3 mM) is dissolved in DMF (4 ml). To the solution is added a sodium methylate solution in methanol (5.17 M/L, 700 μl, 1.1×3.3 mM) and the mixture is stirred for 10 minutes at this temperature. To the mixture are successively added a piece of dry ice and the compound [12] (2 g, 3.3 mM) dissolved in DMF (6 ml), and stirring is continued for 30 minutes. The reaction mixture is poured into water and extracted with methyl ethyl ketone. The extract is washed with 5% aqueous NaHCO3 solution and water, dried over anhydrous magnesium sulfate and concentrated under reduced pressure. The residue is purified by chromatography over silica gel (water content: 10%). Fractions eluted with methyl ethyl ketone are combined and evaporated to dryness under reduced pressure. The residue is triturated with acetone/ether to obtain the title compound of the formula [14] as powder.

Yield: 1.61 g (67%).

IR(Nujol): 3430, 3340, 3170, 1775, 1684, 1645 cm$^{-1}$.

NMR(d-Acetone): 3.45(s,3H), 4.22(m,2H), 4.43(brs, 2H), 5.06(s,1H), 5.10(s,2H), 5.56(s,2H), 5.91(d,J=8,1H), 6.91-7.69(m,18H), 9.04(s,1H).

Part E Anhydrous aluminum chloride (880 mg, 3×2.2 mM) is dissolved in a mixture of anisole (5 ml) and nitromethane (13 ml). While ice-cooling, the powdery compound [14] (1.6 g, 2.2 mM) is added thereto and the mixture is stirred for 45 minutes. The reaction misture is then poured into aqueous NaCHO3 solution (NaHCO3: 3.7 g, 20×2.2 mM; H2O: 20 ml). Precipitates as formed are filtered off, and the aqueous layer is separated from the filtrate and washed with ethyl acetate. After addition of methyl ethyl ketone, the aqueous layer is acidified with 2N hydrochloric acid and saturated with sodium chloride. The organic layer is separated, washed with saturated saline, dried over anhydrous magnesium sulfate and concentrated under reduced pressure. The resultant residue is dissolved in methanol. By addition of ethyl ether to the solution separated out the desired carboxylic acid of the formula [15] as powder. Yield: 634 mg (51%).

IR(KBr): 3440, 3360, 3200, 1779, 1688, 1525 cm$^{-1}$.

UV($\lambda_{max}^{MeOH}$): 273(ε: 10500)nm.

NMR(d6-DMSO): 3.35(s,3H), 3.6-4.6(m,8H), 5.03(s,1H), 5.07(s,2H), 5.47(s,1H), 5.67(bs,1H), 7.2-7.6(m,5H), 7.87(s,1H), 9.30(s,1H).

[α]$_D^{25}$: −89.0°±1.3(c=1.008, MeOH).

Elementary Analysis (C21H23O8N9S)

|  | C | H | N | S |
|---|---|---|---|---|
| Calculated (%): | 44.96 | 4.55 | 21.35 | 5.48 |
| Found (%): | 44.91 | 4.13 | 22.45 | 5.71 |

Part F The carboxylic acid [15] obtained above (470 mg, 0.84 mM) is dissolved in aqueous NaHCO3 solution (NaHCO3: 67 mg, 0.95×0.84 mM; H2O: 8 ml). Lyophilization of the resultant solution gives the sodium salt of the formula [16].

IR(KBr): 3425, 3360, 3200, 1768, 1689, 1659, 1600, 1525 cm$^{-1}$.

UV($\lambda_{max}^{H2O}$): 270(ε: 10900)nm.

NMR(D2O: Ext.TMS): 3.93(s,3H), 4.43-4.85(m,4H), 5.52(s,1H), 5.70(s,2H), 5.78(s,1H), 7.88(s,5H).

[α]$_D^{25}$: −62.1°±1.0(c=1.006, H2O).

Elementary Analysis (C21H22O8N9SNa.2H2O)

|  | C | H | N | S |
|---|---|---|---|---|
| Calculated (%): | 40.71 | 4.23 | 20.35 | 5.18 |
| Found (%): | 40.92 | 4.09 | 20.05 | 5.38 |

EXAMPLE 8

7β-[2-(p-hydroxyphenyl)-2-ureido-acetamido]-7α-methoxy-3-(1-carbamoylmethyl-1H-tetrazol-5-yl)thiomethyl-1-dethia-1-oxa-3-cephem-4-carboxylic acid [Compound No. 20], and its diphenylmethyl ester [Compound No. 19] and sodium salt [Compound No. 21].

Part A

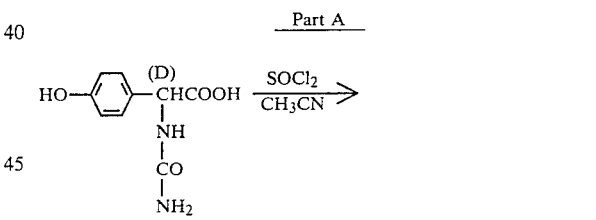

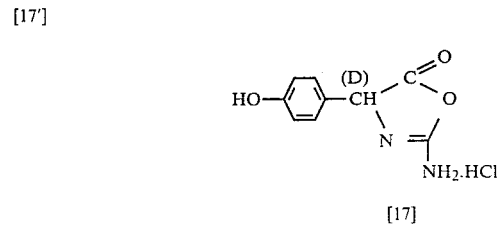

Part B

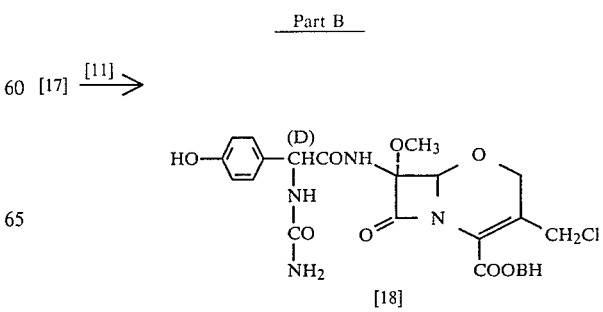

Part C

[18] $\xrightarrow{[13]}$

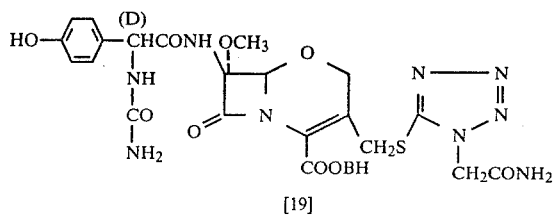

[19]

Part D

[19] $\xrightarrow{AlCl_3}$

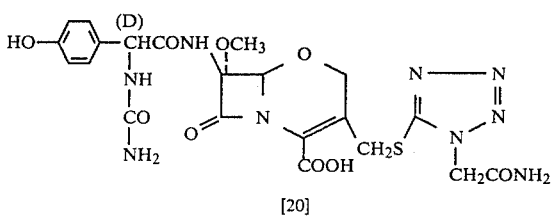

[20]

Part E

[20] $\xrightarrow{NaHCO_3}$

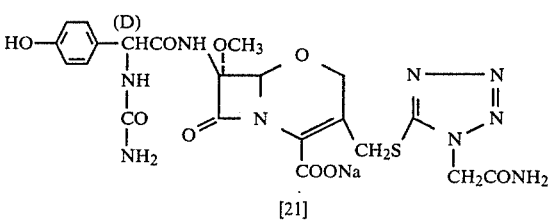

[21]

Part A The starting compound of the formula [17'] (2.88 g, 1.5×9.14 mM) is suspended in acetonitrile (30 ml). After addition of thionyl chloride (1.2 ml, 1.2×1.5×9.14 mM) at −20° C., the suspension is stirred for 30 minutes. By addition of petroleum ether-/ethyl ether (1:1) to the reaction mixture precipitates out the compound of the formula [17], which is known to the art.

Part B To a solution of the compound [11] prepared from the compound [10] (5.0 g) by the method of Example 7 (Part B) in dichloromethane cooling at −50° C. are added DMF (50 ml), propylene oxide (1.27 ml, 2×9.14 mM) and the compound [17] (about 3 g) obtained above. Then the mixture is stirred for one hour while ice-cooling. The reaction mixture is poured into a mixture of water and dichloromethane. The organic layer is separated, washed with aqueous NaHCO₃ and water, dried over anhydrous magnesium sulfate and concentrated under reduced pressure. The residue is purified by chromatography over silica gel (water content: 10%). Fractions eluted with ethyl acetate are combined and evaporated in vacuo. The compound of the formula [18] is thus obtained as a residue. Yield: 781 mg (13.8%).

IR(Nujol): 3430, 3330, 3170, 1778, 1723, 1645 cm$^{-1}$.

NMR(d-Acetone): 3.47(s,3H), 4.42(s,2H), 4.43(ABq-A part,J=12,1H), 4.53(ABq-B part,J=12,1H), 5.13(s,1H), 5.64(s,2H), 6.03(d,J=8.5,1H), 6.70–7.63(m), 6.93(s,1H), 8.43(s,1H), 9.43(s,1H).

Part C The compound of the formula [13] (298 mM, 1.5×1.25 mM) is dissolved in DMF (3 ml). To the solution is added a sodium methylate solution in methanol (5.17 M/L, 314 µl, 1.3×1.25 mM) and the mixture is stirred for 10 minutes. To the mixture are successively added a piece of dry ice and the compound [18] (775 mg, 1.25 mM) dissolved in DMF (3 ml), and stirring is continued for 30 minutes. The reaction mixture is poured into water and extracted with methyl ethyl ketone. The extract is washed with 5% aqueous NaHCO₃ solution and water, dried over anhydrous magnesium sulfate and concentrated under reduced pressure. The residue is triturated with acetone/ethyl ether to obtain the title carboxylic acid of the formula [19] as powder. Yield: 868 mg (93.3%).

IR(Nujol): 3425, 3330, 3180, 1775, 1690, 1650 cm$^{-1}$.

NMR(d-Acetone): 3.47(s,3H), 4.19(ABq-A part,J=12,1H), 4.32(ABq-B part,J=12,1H), 4.47(s,2H), 5.08(s,1H), 5.13(s,2H), 5.52(s,2H), 5.73(d,J=7.5,1H), 6.68–7.97(m), 6.92(s,1H), 8.38(s,1H), 8.81(s,1H).

Part D Anhydrous aluminum chloride (456 mg, 3×1.14 mM) is dissolved in a mixture of anisole (3 ml) and nitromethane (7 ml). While ice-cooling, the powdery compound [19] (845 mg, 1.14 mM) is added thereto and the mixture is stirred for 30 minutes. The reaction mixture is then poured into aqueous NaHCO₃ solution and resultant precipitates are filtered off. An aqueous layer is separated from the filtrate, washed with ethyl acetate, and acidified with 2N hydrochloric acid. The acidic aqueous layer is applied to a column packed with HP-20. Fractions eluted with 40% aqueous acetone are combined, evaporated in vacuo to remove the acetone, and the resultant residue is lyophilized. The title carboxylic acid [20] is thus obtained. Yield: 499 mg (76%).

IR(KBr): 3350, 1775, 1687, 1654, 1612, 1513 cm$^{-1}$.

UV($\lambda_{max}^{MeOH}$): 227.5($\epsilon$: 16600), 274($\epsilon$: 11400)nm.

NMR(d-DMSO): 3.33(s,3H), 4.00–4.45(m,4H), 5.01(s,1H), 5.06(s,2H), 5.33(d,J=8.5,1H), 5.60(s,2H), 6.69(A₂B₂q-A part,J=9,2H), 7.17(A₂B₂q-B part,J=9,2H), 7.54(brs,1H), 7.89(brs,1H), 9.15(s,1H).

$[\alpha]_D^{24}$: −98.0°±1.4(c=1.003, MeOH).

Elementary Analysis (C₂₁H₂₃O₉N₉S.2H₂O)

|  | C | H | N | S |
|---|---|---|---|---|
| Calculated (%): | 41.10 | 4.44 | 20.55 | 5.23 |
| Found (%): | 41.17 | 4.44 | 20.24 | 5.08 |

Part E The carboxylic acid [20] obtained above (400 mg, 0.71 mM) is dissolved in aqueous NaHCO₃ solution (NaHCO₃: 54 mg, 0.9×0.71 mM; H₂O: 8 ml). Lyophilization of the resulting solution gives the sodium salt of the formula [21].

IR(KBr): 3360, 1769, 1688, 1653, 1605, 1513 cm$^{-1}$.

UV($\lambda_{max}^{H_2O}$): 226($\epsilon$: 15300), 270($\epsilon$: 10800)nm.

NMR(D₂O: Ext.TMS): 3.92(s,3H), 4.53(ABq-inside of A part,1H), 4.60(ABq-A part,J=18,1H), 4.70(ABq-inside of B part,1H), 4.79(ABq-B part,J=18,1H), 5.50(s,1H), 5.70(s,2H), 7.32(A₂B₂q-A part,J=9,2H), 7.76(A₂B₂q-B part,J=9,2H).

$[\alpha]_D^{23}$: −68.3°±1.1(c=1.003, H₂O).

Elementary Analysis (C₂₁H₂₂O₉N₉SNa.1.3H₂O)

| | C | H | N | S |
|---|---|---|---|---|
| Calculated (%): | 40.52 | 3.98 | 20.26 | 5.15 |
| Found (%): | 40.87 | 4.16 | 20.07 | 5.06 |

EXAMPLE 9

Alternative synthesis of the compound [3].

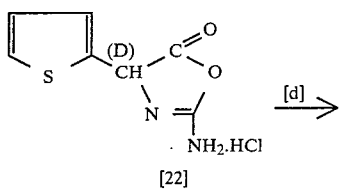

[22]

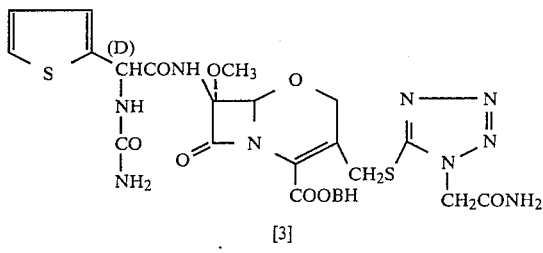

[3]

The compound [d] (412 mg) prepared in Preparation 1 is dissolved in dichloromethane (3 ml). To the solution are added the compound of the formula [22], which has been prepared by reacting D-2-(2-thienyl)-2-ureidoacetic acid (366 mg) with thionyl chloride (180 μl) in acetonitrile (3 ml), DMF (3 ml) and propylene oxide (2 ml), and the mixture is stirred at between −5° C. and −20° C. for one hour. The reaction mixture is washed successively with water, 5% aqueous NaHCO₃ solution and water, dried over anhydrous magnesium sulfate and concentrated in vacuo. The residue is purified by chromatography over silica gel to obtain the desired compound of the formula [3]. The physico-chemical data of the product is identical with that obtained in Example 1.

What is claimed is:

1. A 7β-ureidoacetamido-7α-methoxy-3-(1-carbamoylmethyl-1H-tetrazol-5-yl)thiomethyl-1-dethia-1-oxa-3-cephem-4-carboxylic acid derivative represented by the following formula:

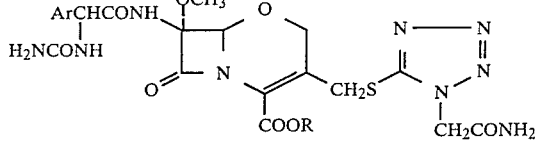

wherein Ar is phenyl, hydroxyphenyl, or thienyl and R is hydrogen, a light metal, or a carboxy-protecting group.

2. A compound as claimed in claim 1 wherein Ar is phenyl or thienyl.

3. A compound as claimed in claim 1 wherein R is hydrogen, sodium, potassium, diphenylmethyl, p-methoxybenzyl, acetoxymethyl, 1-(ethoxycarbonyloxy)ethyl, or pivaloyloxymethyl.

4. Any one of the following compounds:
   7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylic acid,
   sodium 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylate,
   pivaloyloxymethyl 7β-[2-(2-thienyl)-2-ureidoacetamido]-7α-methoxy-3-(1-carbamoylmethyl-1H-tetrazol-5-yl)thiomethyl-1-dethia-1-oxa-3-cephem-4-carboxylate,
   7β-(2-phenyl-2-ureidoacetamido)-7α-methoxy-3-(1-carbamoylmethyl-1H-tetrazol-5-yl)thiomethyl-1-dethia-1-oxa-3-cephem-4-carboxylic acid, and
   sodium 7β-(2-phenyl-2-ureidoacetamido)-7α-methoxy-3-(1-carboxylmethyl-1H-tetrazol-5-yl)thiomethyl-1-dethia-1-oxa-3-cephem-4-carboxylate.

5. A compound as claimed in claim 1 wherein the 7-side chain is in D-form.

6. An antibacterial composition comprising an effective amount of the compound as claimed in claim 1 and conventional carrier.

7. A method for combating bacteria which comprises bringing an effective amount of the compound as claimed in claim 1 to contact with the bacteria.

* * * * *